US008116988B2

(12) United States Patent
Glick et al.

(10) Patent No.: US 8,116,988 B2
(45) Date of Patent: Feb. 14, 2012

(54) METHOD FOR INDEXING NUCLEIC ACID SEQUENCES FOR COMPUTER BASED SEARCHING

(75) Inventors: Benjamin Glick, Chicago, IL (US); William Stokes, Stanton, MI (US)

(73) Assignees: The University of Chicago, Chicago, IL (US); GSL Biotech LLC, Chicago, IL (US)

( * ) Notice: Subject to any disclaimer, the term of this patent is extended or adjusted under 35 U.S.C. 154(b) by 490 days.

(21) Appl. No.: 12/301,547

(22) PCT Filed: May 21, 2007

(86) PCT No.: PCT/US2007/069367
§ 371 (c)(1),
(2), (4) Date: Jan. 28, 2009

(87) PCT Pub. No.: WO2007/137225
PCT Pub. Date: Nov. 29, 2007

(65) Prior Publication Data
US 2009/0270277 A1    Oct. 29, 2009

Related U.S. Application Data

(60) Provisional application No. 60/747,715, filed on May 19, 2006.

(51) Int. Cl.
*G06F 19/00* (2011.01)
*G06F 17/30* (2006.01)

(52) U.S. Cl. .......................................... 702/20; 707/711

(58) Field of Classification Search ........................ None
See application file for complete search history.

(56) References Cited

U.S. PATENT DOCUMENTS

2006/0155479 A1*   7/2006   Knowles et al. ................. 702/19

FOREIGN PATENT DOCUMENTS

WO    WO 2007/137225    11/2007

OTHER PUBLICATIONS

Bernal et al. Genomes OnLine Database (GOLD): a monitor of genime projects world-wide. Nucleic Acids Research vol. 29, pp. 126-127 (2001).*

Miyata et al. Identification of a Novel GC-Rich 113-Nucleotide Region to Complete the Circular, Single-Stranded DNA Genome of TT Virus, the First Human Corcovirus. Journal of Virology vol. 73, pp. 3582-3586 (1999).*
Abouelhoda, M.I. et al., "Replacing suffix trees with enhanced suffix arrays," J. Discrete Algorithms (2004) 2:53-86.
Altschul, S.F. et al., "Basic local alignment search tool," J. Mol. Biol. (1990) 215:403-410.
Altschul, S.F. et al., "Gapped BLAST and PSI-BLAST: a new generation of protein database search programs," Nuc. Acids Res. (1997) 25:3389-3402.
Edgar, R.C., "Muscle: multiple sequence alignment with high accuracy and high throughput," Nuc. Acids Res. (2004) 32(5):1792-1797.
Greene, W.A., "k-way merging and k-ary sorts," In 31st Annual ACM Southeast Conference, 1993, Birmingham, Alabama (1993) 127-135.
Hunt, E., "The suffix sequioa index for approximate string matching," DCS Tech Report, Department of Computing Science, University of Glasgow, http://www.dscglaacuk/publications/PAPERS/7185/TR-2003-135pdf (2003) 1-26.
Kent, W.J., "BLAT—the BLAST-like alignment tool," Genome Res. (2002) 12:656-664.
Kurtz, S. et al., "Versatile and open software for comparing large genomes," Genome Biol. (2004) 5(2):R12.1-12.9.
Li, M. et al., "Patternhunter II: Highly sensitive and fast homology search," J. Bioinform. Comput. Biol. (2004) 2:417-439.
Ning, A. et al., "SSAHA: a fast search method for large DNA databases," Genome Res. (2001) 11:1725-1729.
Ning, Z. et al., "The SSAHA trace server," Proceedings of the 2004 IEEE Computational Systems Bioinformatics Conference (CSB 2004) 2004:544-545.
Noe, L. et al., "Improved hit criteria for DNA local alignment," BMC Bioinformatics (2004) 5:149, 9 pages.
Pearson, W.R. et al., "Improved tools for biological sequence comparison," Proc. Natl. Acad. Sci. USA (1988) 85:2444-2448.
Price, A.L. et al., "Whole-genome analysis of Alu repeat elements reveals complex evolutionary history," Genome Res. (2004) 14:2245-2252.
Wu, T.D. et al., "GMAP: a genomic mapping and alignment program for mRNA and EST sequences," Bioinformatics (2005) 21:1859-1875.
International Search Report and Written Opinion for Application No. PCT/US07/69367 dated Aug. 7, 2008 (8 pages).

* cited by examiner

*Primary Examiner* — John S Brusca
(74) *Attorney, Agent, or Firm* — Michael Best & Friedrich LLP (57) ABSTRACT

The present invention relates to a method for indexing nucleic acid sequences to aid computer based searching of nucleic acid sequences by indexing a nucleotide sequence by the presence of unique Kmers in the sequence. The method of the present invention comprises utilizing an algorithm to automatically index a nucleic acid sequence.

10 Claims, 5 Drawing Sheets

MICA File Structure and Data Storage Requirements

| File Element | Generic Storage Requirement (bytes) | Storage Requirement for Chromosome 1 (bytes) |
|---|---|---|
| Sequence Segment | | |
| A. Segment Format | 1 | 1 |
| B. Segment Size | 4 | 4 |
| C. Sequence Properties | 1 | 1 |
| D. DNA Sequence | $L$ | 245,522,847 (234 MB) |
| SEGMENT TOTAL | $6 + L$ | 245,522,853 (234 MB) |
| Index Segment | | |
| E. Segment Format | 1 | 1 |
| F. Segment Size | 4 | 4 |
| G. Index Properties | 1 | 1 |
| H. Chunk Counts Summary | $4^{K+1}$ | $K = 4$: 1,024 (1 KB) <br> $K = 6$: 16,384 (16 KB) |
| I. Degenerate $K$-mer Count | 4 | 4 |
| J. N-Stretch Count ($S$) | 4 | 4 |
| K. Chunk Data Array | ($4^K * C$ + number of nondegenerate $K$-mers) * 2 | $K = 4$: 447,573,936 (427 MB) <br> $K = 6$: 476,350,748 (454 MB) |
| L. Degenerate Data Array | (number of partially degenerate $K$-mers) * $(4 + K)$ | $K = 4$: 1,752 (1.7 KB) <br> $K = 6$: 3,650 (3.6 KB) |
| M. N-Stretch Data Array | $8S$ | 296 |
| SEGMENT TOTAL | Typically about $2L$ bytes. | $K = 4$: 447,577,022 (427 MB) <br> $K = 6$: 476,371,092 (454 MB) |

FIG. 1

Representative Sizes, Creation Times, and Loading Times for MICA Indexes

| | K | Index Size (GB) | Index Creation Time (sec) | Index Loading Time (sec) |
|---|---|---|---|---|
| Chromosome 1 ($2.46 \times 10^8$ bases) | 4 | 0.42 | 19.3 | 0.023 |
| | 6 | 0.44 | 27.1 | 0.024 |
| Random Sequence ($2.46 \times 10^8$ bases) | 4 | 0.46 | 23.5 | 0.020 |
| | 6 | 0.49 | 32.0 | 0.025 |
| Human Genome ($3.08 \times 10^9$ bases) | 4 | 5.33 | 262 | 0.49 |
| | 6 | 5.67 | 345 | 0.44 |

FIG. 2

Representative Search Times for $K = 4$

| Query | Chromosome 1 | | Human Genome | |
|---|---|---|---|---|
| | Time (sec) | Hits | Time (sec) | Hits |
| Nondegenerate 3-mers | 0.82 [0.51] | $6.96 \times 10^6$ | 11.5 | $8.90 \times 10^7$ |
| Nondegenerate 4-mers | 0.13 [0.028] | $1.69 \times 10^6$ | 2.5 | $2.17 \times 10^7$ |
| Nondegenerate 6-mers | 0.35 [0.11] | 160,702 | 5.8 | $2.05 \times 10^6$ |
| Nondegenerate 8-mers | 0.38 [0.11] | 16,631 | 6.2 | 213,099 |
| Nondegenerate 15-mers | 0.56 [0.11] | 1.39 | 9.0 | 5.81 |
| Nondegenerate 30-mers | 0.54 [0.10] | 1.03 | 8.3 | 1.24 |
| Nondegenerate 100-mers | 0.41 [0.069] | 1.01 | 6.1 | 1.02 |
| Nondegenerate 1000-mers | 0.14 [0.019] | 1.00 | 2.3 | 1.00 |
| *Alu* 30-mer fragment | 0.77 [0.095] | 1,130 | 13.6 | 14,041 |
| GDGCHC (*Bsp1286*I) | 0.43 [0.11] | 398,999 | 6.9 | 4,776,086 |
| GCCNNNNNGGC (*Bgl*I) | 0.37 [0.12] | 44,761 | 6.1 | 520,776 |
| ACNNNNGTAYC (*Bae*I) | 1.55 [0.34] | 20,243 | 23.2 | 259,837 |

FIG. 3

Representative Search Times for $K = 6$

| Query | Chromosome 1 | | Human Genome | |
|---|---|---|---|---|
| | Time (sec) | Hits | Time (sec) | Hits |
| Nondegenerate 3-mers | 1.1  [0.80] | $6.96 \times 10^6$ | 14.8 | $8.90 \times 10^7$ |
| Nondegenerate 4-mers | 0.28  [0.16] | $1.69 \times 10^6$ | 4.2 | $2.17 \times 10^7$ |
| Nondegenerate 6-mers | 0.043 [0.0032] | 160,702 | 0.96 | $2.05 \times 10^6$ |
| Nondegenerate 8-mers | 0.079  [0.011] | 16,631 | 1.6 | 213,099 |
| Nondegenerate 15-mers | 0.088 [0.0074] | 1.39 | 1.8 | 5.81 |
| Nondegenerate 30-mers | 0.13 [0.0076] | 1.03 | 1.8 | 1.24 |
| Nondegenerate 100-mers | 0.12 [0.0050] | 1.01 | 1.7 | 1.02 |
| Nondegenerate 1000-mers | 0.094 [0.0023] | 1.00 | 1.3 | 1.00 |
| *Alu* 30-mer fragment | 0.12 [0.0055] | 1,130 | 2.5 | 14,041 |
| GDGCHC (*Bsp1286*I) | 0.13  [0.031] | 398,999 | 2.5 | 4,776,086 |
| GCCNNNNNGGC (*Bgl*I) | 0.44  [0.15] | 44,761 | 6.2 | 520,776 |
| ACNNNNGTAYC (*Bae*I) | 1.40  [0.37] | 20,243 | 21.1 | 259,837 |

METHOD FOR INDEXING NUCLEIC ACID SEQUENCES FOR COMPUTER BASED SEARCHING

CROSS-REFERENCE TO RELATED APPLICATIONS

This patent application is a national stage filing under 35 U.S.C. 371 of International Application No. PCT/US07/69367, filed May 21, 2007, which claims priority benefits to U.S. Provisional Patent Application No. 60/747,715, filed May 19, 2006.

BACKGROUND OF THE INVENTION

Researchers in the Biotechnology industry are increasingly working with very large DNA databases. For example, the human genome is approximately 3 gigabases. Searching these databases has traditionally been done with dedicated servers because the search algorithms require substantial computer resources. As an alternative analysis tool, desktop computers are often more versatile and convenient, and they are now routinely equipped with hundreds of gigabytes (GB) of hard disk space and several GB of RAM (random access memory). The challenge is to harness this capacity by creating DNA analysis software that works efficiently in a multi-purpose desktop environment.

A basic requirement for DNA analysis software is rapid searching of a DNA database to find all exact matches for a query sequence. The desired search speeds can only be achieved by indexing the database. One well-characterized indexing strategy is to generate a suffix tree (Gusfield, D., Algorithms on Strings, Trees, and Sequences: Computer Science and Computational Biology. Cambridge University Press, Cambridge, 1997, incorporated herein by reference). Although suffix trees have been used productively for some molecular biology applications, such as aligning whole genomes (Kurtz, S., A. Philippy, A. L. Delcher, M. Smoot, M. Shumway, C. Antonescu, and S. L. Salzberg, Versatile and open software for comparing large genomes. Genome Biol. 5: R12, 2004, incorporated herein by reference), they consume large amounts of memory, up to 15 bytes or more per base. More compact than suffix trees are suffix arrays, which can provide similar search capabilities while requiring only 4-8 bytes per base (Abouelhoda, M. I., S. Kurtz, and E. Ohlebusch, Replacing suffix trees with enhanced suffix arrays. J. Discrete Algorithms 2: 53-862004, 2004, incorporated herein by reference).

Non-suffix-based indexing strategies are currently in more widespread use for DNA databases. The SSAHA algorithm divides a DNA sequence into nonoverlapping K-mers of K consecutive bases (a K-mer is an oligonucleotide of length K), and stores the position of these K-mers in a hash table (Ning, A., A. J. Cox, and J. C. Mullikin, SSAHA: a fast search method for large DNA databases. Genome Res. 11: 1725-1729, 2001, incorporated by reference). A similar indexing method is used by the BLAT algorithm (Kent, W. J, BLAT—The BLAST-like alignment tool. Genome Res. 12: 656-664, 2002, incorporated by reference). Both SSAHA and BLAT generate small indexes, on the order of 1 byte or less per base, and they can be orders of magnitude faster than BLAST or FASTA, which index the query sequence rather than the database (Pearson, W. R. and D. J. Lipman, 1988, Improved tools for biological sequence comparison. Proc. Natl. Acad. Sci. USA 85: 2444-2448; Altschul, S. F., W. Gish, W. Miller, E. W. Myers, and D. J. Lipman, 1990, Basic local alignment search tool. J. Mol. Biol. 215: 403-410; Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. Nucleic Acids Res. 25: 3389-3402, each reference incorporated by reference). SSAHA and BLAT have proven to be powerful for applications such as mapping sequence reads to a genome, or aligning mRNA sequences with the corresponding genomic DNA sequences. However, SSAHA and BLAT have limitations. Unlike suffix-based algorithms, which can identify all matches to any query sequence, SSAHA cannot detect a match of fewer than K bases, and requires 2K−1 consecutive matching bases to guarantee that a match will be registered. Because SSAHA sorts the search results, efficient searching is achieved by ignoring the K-mers that occur most frequently in the database. Similarly, BLAT sacrifices completeness for speed.

These various algorithms have generally been designed with the assumption that the complete index of a DNA database will be stored in main memory. Such algorithms are inconvenient for desktop applications, because an index might occupy much or all of the memory of a typical personal computer.

SUMMARY OF THE INVENTION

Molecular biologists work with databases representing DNA molecules that range in size from plasmids to chromosomes. A common requirement is to search a DNA database to find exact matches for a nondegenerate or partially degenerate query. The software programs available for such purposes normally run on remote servers, but because desktop computers are increasing in power, an appealing alternative is to work with DNA databases stored on local computers. The present invention provides a method for rapidly indexing a DNA database. The method makes use of a data structure algorithm called MICA (K-Mer Indexing with Compact Arrays). The indexes occupy only ~2 bytes per base and can be generated quickly. Unlike most other algorithms, MICA indexes not only the standard nucleotide base characters A, C, G, and T, but also the degenerate base characters B, D, H, K, M, R, S, V, W, Y, and N. Efficient search procedures identify all matches for a nondegenerate or partially degenerate query of any length. When a file is being searched, only a fraction of the index is present in memory at any given time, so desktop computers with modest amounts of RAM can search large databases efficiently.

MICA rapidly indexes a DNA database. On a Macintosh G5 computer, the complete human genome could be indexed in about 5 minutes. The indexing algorithm recognizes all 15 base characters: A (which represents adenine), C (which represents cytosine), G (which represents guanine), and T (which represents thymine), but also the degenerate base characters B (which represents C, G or T), D (which represents A, G or T), H (which represents A, C or T), K (which represents G or T), M (which represents A or C), R (which represents A or G), S (which represents C or G), V (which represents A, C or G), W (which represents A or T), Y (which represents C or T), and N (which represents A, C, G or T). For a typical sequence of length L, the index occupies only about 2 L bytes. The index can be searched to return a complete list of exact matches for a nondegenerate or partially degenerate query of any length. A typical search of a long DNA sequence involves reading only a small fraction of the index into memory. As a result, searches are fast even when the available RAM is limited.

In one embodiment, the present invention provides a method of indexing and recording a nucleotide sequence with a computer to create a file. The method comprises selecting a nucleotide sequence to index and having a computer scan the nucleotide sequence, identifying each occurrence of a base sequence of a selected base width K. The computer then determines all of the unique base sequences of width K in the nucleotide sequence, each unique base sequence of width K being a K-mer. A K-mer can either be a non-degenerate sequence comprised solely of the bases A, C, G, and T, or a partially degenerate sequence comprised of the non-degenerate DNA bases A, C, G, and T plus the degenerate bases R, Y, M, K, S, W, H, B, V, D and N. A partially degenerate sequence contains fewer than K instances of the completely degenerate base N.

In one embodiment, the computer divides the nucleotide sequence into C separate chunk sections, where C is an integer. In one embodiment, each chunk section consists of X bases, where C is an integer less than 65,536 and C is an integer equal to L/X or the next integer greater than L/X, where L is the length of the nucleotide sequence. In another embodiment, C is an integer equal to L/65,535 or the next integer greater than L/65,535.

The computer records in the file the position of each K-mer in the nucleotide sequence. The position of each non-degenerate K-mer is recorded in a non-degenerate data array in the file. In one embodiment, the non-degenerate data array is divided into $4^K$ partitions corresponding to all of the possible $4^K$ non-degenerate K-mers. Each partition contains a list of integers representing the number of times a particular non-degenerate K-mer is present in each of the chunk sections, followed by a list of integers representing intra-chunk section positions of the particular K-mer in each of the chunk sections. The position of each partially degenerate K-mer is recorded in a degenerate data array in the file. Each particular partially degenerate K-mer is represented as an integer that marks the absolute position of the particular K-mer, followed by a string that encodes the sequence of the particular K-mer.

The computer also determines the number of times each non-degenerate K-mer appears in the nucleotide sequence and records this information in a chunk count summary field. The computer also determines the total number of partially degenerate K-mers in the nucleotide sequence and records this number in a degenerate K-mer count field. The computer also determines the number of separate stretches of K or more consecutive base N's in the nucleotide sequence and records this information an N-stretch count field.

In another embodiment, the invention provides a data structure for recording information regarding a nucleic acid, the information being stored in a computer file. The data structure contains information on the K-mer's of the nucleotide sequence. The data structure comprises a non-degenerate data array containing the position of each particular non-degenerate K-mer of a nucleotide sequence; a degenerate data array containing the position of each particular partially degenerate K-mer and a string encoding the sequence of each particular partially degenerate K-mer; a sequence segment format field that contains an integer identifying this segment as the sequence segment; a sequence segment size field containing an integer representing the total number of bytes occupied by the sequence segment; a sequence properties field containing an integer representing the topology and the strandedness of the nucleotide sequence; a DNA sequence field containing the base sequence of the nucleotide sequence; an index segment format field that contains an integer identifying this segment as the index segment; an index segment size field containing an integer representing the total number of bytes occupied by the index segment; an index properties field containing an integer representing the byte order of the index; a chunk counts summary field containing a list of integers representing the total number of times a particular non-degenerate K-mer appears in the nucleotide sequence; a degenerate K-mer count field containing an integer representing the total number of partially degenerate K-mers in the nucleotide sequence; an N-stretch count field containing an integer S representing the number of separate stretches of K or more consecutive N's in the nucleotide sequence; and an N-stretch data array containing S pairs of integers that represent the starting positions and lengths of the separate stretches of consecutive N's in the nucleotide sequence.

In another embodiment of the invention, the invention provides a method of searching for a specific base sequence in a nucleotide sequence using a computer. In one embodiment, the invention comprises using a computer to access the data structure of the invention containing information on a nucleotide sequence and having the computer search the information in the data structure for the presence and location of the specific base sequence. The computer accesses a data structure file of the present invention containing information on the nucleotide sequence desired. The computer then loads the data from the index segment format field, the index segment size field, the index properties field, the chunk counts summary field, the degenerate K-mer count field and the N-stretch Count field into main memory. The computer then divides the specific base sequence that is being searched for into specific K-mers. The computer accesses the data loaded into the main memory and the information in the degenerate data array, the non-degenerate data array, and the N-stretch data array and uses this information to generate the position of the unique K-mers in the nucleotide sequence. The computer then uses this K-mer position data to determine the location of the specific base sequence in the nucleotide sequence if present.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION OF THE INVENTION

The present invention relates to a method for indexing nucleic acid sequences to aid computer based searching of nucleic acid sequences. The method of the present invention comprises utilizing an algorithm to automatically index a nucleic acid sequence. This algorithm is suitably utilized by a software program running on a computer. The invention also comprises a data structure which comprises an indexed nucleotide sequence. The data structure can be saved as a computer file.

The term "computer file", as used herein, refers to a stream (sequence) of bits stored as a single unit, typically in a file system on electronic storage medium such as a computer disk, a computer hard drive, a CD-ROM, a DVD-ROM or a magnetic tape. While a file is usually presented as a single stream, it can be, and is most often, stored as multiple fragments of data at different places on a disk or hard drive (or even multiple disks). The file can be in any format suitable for the program accessing the file, and suitable for the operating system the program is operating on.

The term "computer readable storage medium" and "permanent storage", as used herein, refers to any medium that can store data that is accessible by a computer. This includes, but is not limited to, a computer disk, a computer hard drive, a CD-ROM, a DVD-ROM or a magnetic tape. The term "main memory" or "resident memory" as used herein refers to the RAM memory of a computer.

The term "data structure", as used herein, refers to an organization structure in which data is stored on either a computer readable storage medium, or in the resident memory of a computer. The organization structure allows different pieces of data to be organized by different identifiers such as a field.

The term "field", as used herein, refers to a particular area of the data structure or record in which the same type of information is regularly recorded. For example, a date has three distinct fields: the day, the month, the year. Identifier labels have been placed in front of the term "field" in order to distinguish a specific field from other fields in the claims. These labels do not impart any specific functionality to the field, they simply label the field for ease of reference. The identifier usually indicates the type of data stored in the field, therefore a "Segment Format" field contains information in the field that indicates the format of a of a file segment.

The term "nucleic acid", as used herein refers to any molecule that contains a nucleotide chain. This includes, but is not limited to, single or double stranded DNA, RNA, plasmids, chromosomes and nucleic acid fragments.

In the present invention, a nucleic acid sequence is indexed by scanning the sequence with a window of a selected width K (width being the number of bases). Each sequence of width K that has a specific combination of bases is a unique K-mer. Each unique K-mer is repeated multiple times in a sequence. For example, when K=4, examples of some unique K-mers could be ACCT, ACTG, ACTT, TCGA, TTCG, etc., with each of these unique K-mers being repeated multiple times in a DNA sequence. For a sequence of length L, sliding the window one base at a time yields L−K+1 overlapping K-mers. A MICA index uses arrays to store all of the positions for each K-mer in the subject nucleic acid sequence. Because chromosomal DNA molecules can be up to several hundred million bases long, the K-mer position values would normally be represented as 4-byte integers. The present invention reduces this data storage requirement by dividing the sequence into "chunks." Suitably a sequence is divided into C separate "chunks" of 65,535 ($2^{16}$−1) bases, where C=ceiling (L/65,535). The number of instances of each K-mer within a given chunk can range from 0 to 65,535, so a 2-byte integer can be used to record this number. Other choices are possible for the bases per chunk as long as this value is less than $2^{16}$, although reducing this value below 65,535 would increase the file size. The intra-chunk positions of each non-degenerate K-mer are stored as 2-byte integers. The absolute positions of a K-mer within a full DNA sequence can then be calculated with the aid of a list specifying the number of instances of the K-mer within each chunk.

A non-degenerate K-mer consists of a combination of the four non-degenerate base characters A, G, C and T. A partially degenerate K-mer is comprised of the non-degenerate bases A, G, C and T plus the degenerate bases B, D, H, K, M, R, S, V, W, Y and N where a partially degenerate sequence contains fewer than K instances of the completely degenerate base N. A fully degenerate K-mer consists only of the base N. Partially degenerate K-mers must be recognized if the index is to capture all of the information in any nucleic acid sequence. It would be wasteful to create an array for all of the different partially degenerate K-mers because most of the array elements would typically be empty. Instead, for each partially degenerate K-mer that is actually present in a subject sequence, the present invention uses a 4-byte integer to record the absolute position of the K-mer, followed by a K-byte string to record the sequence of the K-mer. This approach is inefficient with regard to data storage, but most nucleic acid sequences contain very few partially degenerate K-mers, and the simplicity of the data format facilitates searching. A separate strategy is used for stretches of N's, which are commonly used to indicate undefined portions of a sequence. Here S designates the number of "N-stretches" of K or more consecutive N's. MICA efficiently indexes N-stretches by recording their starting positions and their lengths.

Also stored in the index is the topology of the subject nucleic acid molecule (linear or circular). With circular nucleic acid molecules, MICA finds matching sequences that span the numerically defined origin.

Figure 1:
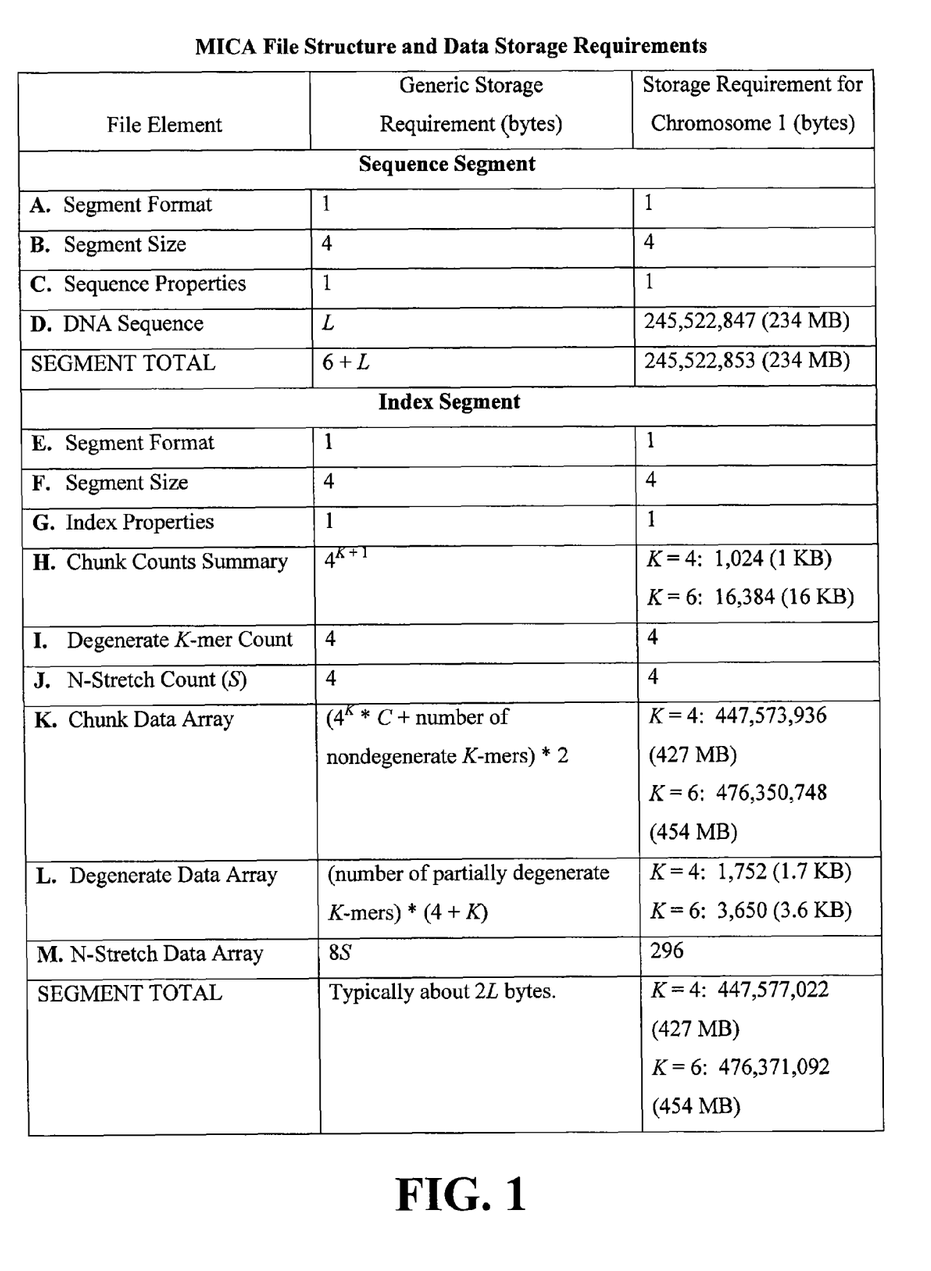
FIG. 1 is a table the depicts the index structure and data storage requirements of the invention.

FIG. 1 summarizes the MICA file structure, together with the generic data storage requirements for each part of the file. As an example, FIG. 1 lists the specific data storage requirements for human chromosome 1, which at ~246 million bases represents one of the longest DNA molecules that needs to be indexed. To ensure that memory addresses can be represented as 4-byte integers, MICA has been constrained to index individual DNA sequences of no more than 1 gigabase.

The main body of a MICA index is the Chunk Data Array, which stores the positions of the nondegenerate K-mers (FIG. 1). The total number of position values is largely independent of K. However, there are $4^K$ different nondegenerate K-mers, so the Chunk Data Array is divided into $4^K$ partitions. Each partition is divided into C sub-partitions that contain the intra-chunk position values. The sizes of these sub-partitions are recorded in a list at the beginning of the partition. As a result, the practical upper limit for K is 7, because for K=8 there would be 65,536 sub-partitions per chunk, and the lists of sub-partition sizes would occupy more space than the lists of K-mer position values. The practical lower limit for K is 3, because reducing K increases the size of the partitions that must be read from disk, thereby slowing most searches.

To create a MICA index, a subject nucleic acid sequence in FASTA format (FASTA format description ncbi.nlm.nih.gov/BLAST/fasta.shtml) is scanned using a window of width K. Both uppercase and lowercase characters are recognized. A MICA file consists of a Sequence Segment (containing values for the following fields: Segment Format, Segment Size, Sequence Properties, and the DNA Sequence (elements A-D of FIG. 1)) followed by an Index Segment (containing values for the following fields: Index Segment Format, Index Segment Size, Index Properties, Chunk Counts Summary, degenerate K-mer Count, N-Stretch Count (S), Chunk Data Array, Degenerate Data Array, and N-Stretch Data Array (elements E-M in FIG. 1)).

With respect to the Sequence Segment, for the Segment Format, a single byte is used to specify the format, identifying this segment as the sequence segment. For the Segment Size, the size is specified by a 4 byte integer. For the Sequence Properties, a single byte is used to record properties of the sequence, including its topology (linear or circular) and its strandedness (single- or double-stranded). For the DNA Sequence, the sequence is stored as a string of uppercase ASCII characters.

With respect to the Index Segment, for the Index Segment Format, a single byte is used to specify the format, identifying this segment as the index segment. For the Index Segment Size, the size is specified by a 4-byte integer. For the index Properties, a single byte is used to record the byte order ("endianness") of the index. This byte order can be either "Big Endian", meaning that the high-order byte of a multi-byte number is stored in memory at the lowest address while the low-order byte is stored at the highest address, or "Little Endian", meaning that the low-order byte of a multi-byte number is stored in memory at the lowest address while the high-order byte is stored at the highest address. If the byte order is opposite to that of the machine being used to run the queries, MICA corrects the byte order when processing the index data. The Chunk Counts Summary is a list of $4^K$ 4-byte integers representing the total number of times each nondegenerate K-mer appears in the sequence. For the MICA index, the 4-base nondegenerate DNA alphabet is arranged in the order G, A, T, C. Thus, the first nondegenerate K-mer listed is GGGG (K=4) or GGGGGG (K=6), and the last one listed is CCCC (K=4) or CCCCCC (K=6). This lexicographical order yields contiguous index reads for K-mers that end in the most common partially degenerate bases: R (A or G), Y (C or T), and W (A or T). The Degenerate K-mer Count is a 4-byte integer representing the total number of partially degenerate K-mers in the sequence. The N-Stretch Count S is a 4-byte integer representing the number of separate stretches of K or more consecutive N's. The Chunk Data Array is divided into 4 partitions corresponding to the $4^K$ nondegenerate K-mers. Each partition contains a list of 2-byte integers representing the number of times the K-mer is present in each of the C chunks, followed by a list of 2-byte integers representing the intra-chunk positions of the K-mer in each of the C chunks. The first partition contains the data for GGGG (K=4) or GGGGGG (K=6), and the second partition contains the data for GGGA (K=4) or GGGGGA (K=6), and so on. The Degenerate Data Array is a list of the partially degenerate K-mers. Each partially degenerate K-mer is represented as a 4-byte integer that marks the absolute position of the K-mer, followed by a K-byte string that encodes the sequence of the K-mer. The N-Stretch Data Array consists of S pairs of 4-byte integers that represent the starting positions and lengths of the N-stretches.

If a sequence occupies more than a predetermined number of chunks, suitably, but not limited to 16 chunks, then loading of a MICA index consists of reading the values of the Segment Format, Segment Size, Sequence Properties, skipping over the DNA sequence, and reading the values of the Index Segment Format, Index Segment Size, Index Properties, Chunk Counts Summary, degenerate K-mer Count, and N-Stretch Count (S) of the Index Segment. The parameters for human chromosome 1 were: L=245,522,847 bases; C=3,747 chunks; S=37 N-stretches (total of 22,695,000 N's).

An initial scan fills in the data for index elements Index Segment Format, Index Segment Size, Index Properties, Chunk Counts Summary, degenerate K-mer Count, and N-Stretch Count (S) (See FIG. 1). Then the appropriate memory for the data arrays (index elements Chunk Data Array, Degenerate Data Array, and N-Stretch Data Array) is allocated, and a second scan fills in the positions of the K-mers and N-stretches. These operations are fast, partly because building the index requires no sorting. If sufficient memory is available, indexing speed is maximized by building the entire index in memory and then writing to disk in a single step. In the case of human chromosome 1, this process requires about 0.67 GB of RAM, an amount that is available on many desktop computers. If memory is limiting, only a subset of the K-mer position values are stored in memory at a given time, and the index is written to disk in multiple steps.

MICA can then embed a copy of the DNA sequence within the file. This sequence consists of characters in 8-bit ASCII format, and therefore occupies L bytes. The original sequence file can then be dispensable for searching. In another embodiment, MICA can be integrated with software that automatically generates a suitably formatted DNA sequence.

If a DNA sequence occupies more than a predetermined number of chunks, suitably, but not limited to 16 chunks (~1 megabase), only the values from the Segment Format, Segment Size, Sequence Properties, Index Segment Format, Index Segment Size, Index Properties, Chunk Counts Summary, degenerate K-mer Count, and N-Stretch Count (S) fields of the MICA file are initially read from disk. These reads are very fast because they involve a small amount of data, just over 1 KB for K=4 or just over 16 KB for K=6. During a search, MICA uses the data from this first portion of the index to find the relevant position values. For example, to find the positions of a nondegenerate K-mer, an entry in the Chunk Counts Summary indicates where the relevant position values can be read from the Chunk Data Array. Thus, MICA selectively reads only the essential data from disk, thereby performing efficient I/O operations and minimizing RAM usage.

The query length Q can range from one base to the length of the subject DNA sequence. Both strands of the DNA molecule are searched. For a query that is palindromic—i.e., identical to its reverse complement—a single search is performed. For a query that is nonpalindromic, two successive searches are performed, one with the query and another with the reverse complement of the query. If the DNA molecule is circular, the initial search is followed by a secondary search for matches that span the origin. One step in this secondary search involves dividing the query in half and then checking for one of two possibilities: either the first half-query matches within the last Q–1 bases of the DNA sequence, or the second half-query matches within the first Q–1 bases of the DNA sequence.

If a query is shorter than K bases, it is extended to K bases by adding N's, and is then treated as being partially degenerate (see below). If a query is exactly K bases, the search consists of converting the 2-byte intra-chunk position values for that K-mer to 4-byte absolute position values. If a query is longer than K bases, it is decomposed into constituent K-mers, which are examined as follows. The list of intra-chunk position values for the first K-mer is read from the index and converted to absolute position values, thereby creating an initial working list. Each value in the working list is then compared with the second K-mer list. The result is a new working list, which indicates where both the first and second K-mers from the query match the subject DNA sequence. This new working list is then compared with the next K-mer list, and so on. In this manner, MICA progressively trims the initial working list to generate a final list of matches.

With a query longer than K bases, the constituent K-mers are examined in increasing order of their frequency of appearance in the subject DNA sequence. For example, a search for the 12-mer AAAACCCCGGGG using K=4 might involve calculating the positions for CCCC, then comparing each CCCC position against the list of positions for GGGG, then comparing each CCCCGGGG position against the list of positions for AAAA, which in this case would be the most common of the three 4-mers. This strategy of starting with the rarest K-mer can significantly accelerate searches because some K-mers are found less frequently than others and therefore result in fewer comparisons. In chromosome 1, the most common 4-mer (AAAA) appears 56 times more often than the rarest 4-mer (CGCG), and the most common 6-mer (TTTTTT) appears 929 times more often than the rarest 6-mer (CGTACG).

Each successive K-mer search is limited to the range of chunks that generated hits for the current working list. In the example above, after the CCCCGGGG hits have been identified, the search for AAAA is limited to the chunks between the first and last occurrence of CCCCGGGG. If a working list contains no hits, the search is terminated. This range limitation method can accelerate searches when a query has a small number of matches to the subject sequence.

A partially degenerate query can be expanded by searching for all of the possible matching sequences. For example, the restriction enzyme Bsp1286I has the recognition sequence GDGCHC, which can potentially match 9 nondegenerate sequences (when the second base is A, G, or T, and the fifth base is A, C, or T) and 40 partially degenerate sequences (when the second base is D, R, K, or W, or the fifth base is H, M, Y, or W). A search for GDGCHC will therefore return matches for all of the 49 possible matching 6-mers. Alternatively, searches for a partially degenerate query can be restricted to return only literal matches to that character string, so a search for "GDGCHC" will return matches only for the single 6-mer GDGCHC.

MICA scans a partially degenerate query to determine an efficient search strategy that limits the degeneracy of the constituent K-mers. For example, the restriction enzyme BaeI has the recognition sequence ACNNNNGTAYC, and for K=4 the matches are found by searching for GTAY, TAYC, and ACNN. The MICA index is ordered lexicographically, so the K-mer ACNN invokes 16 contiguous disk reads from the Chunk Data Array, whereas the equivalent K-mers NNAC and NACN would invoke non-contiguous reads. Because contiguous reads are faster than non-contiguous reads, MICA pushes any degeneracy to the end of a K-mer whenever possible.

With a partially degenerate K-mer, the working list must be compared to multiple individual K-mer lists using an intersection algorithm. An obvious approach would be to adapt the method that is used with a single nondegenerate K-mer. In that case, MICA finds the intersection of the working list and the next K-mer list using a standard technique: a pointer is assigned to the K-mer list, and for each successive element in the working list, the pointer is advanced until the value in the K-mer list equals or exceeds the value in the working list (See Knuth D E: The Art of Computer Programming. Volume 3: Sorting and Searching, 2nd edn: Addison-Wesley; 1998 incorporated herein by reference). When there are multiple K-mer lists, a pointer can be assigned to each one, and a working list element can be compared to all of the K-mer lists. However, this method becomes very inefficient if the working list is larger than the individual K-mer lists, because most of the comparisons fail to advance the pointers. MICA therefore uses an alternative intersection algorithm for partially degenerate K-mers. A boolean array of 65,535 elements is used to represent the positions in a chunk. For a given chunk, all of the individual K-mer lists are scanned, and the 2-byte position values are recorded by setting the corresponding boolean elements to true, yielding a boolean array that indicates which positions in the chunk match one of the K-mers. Then the intersection is obtained by checking whether each working list element corresponds to a value of true in the boolean array. This method is efficient due to the relatively small number of operations and the sequential nature of the memory accesses.

When a K-mer is very degenerate, a substantial amount of time may be needed to read and process the index data. In such cases, MICA switches to an alternate mode that uses the embedded DNA sequence. The entire query is compared to DNA sequence fragments that overlap each hit in the working list. MICA can be configured to perform this mode switch whenever the amount of index data that would need to be read exceeds a set percentage of a total DNA sequence. Such a suitable percentage could be 33% of the total DNA sequence data, but could suitably be any other desired percentage. This condition typically arises with extremely degenerate K-mers such as ANNN (K=4) or ANNNNN (K=6). Even with a less degenerate K-mer, the alternate mode is used if more data would be read by using the index than by directly examining the DNA sequence. Thus, at each stage of a search, MICA takes advantage of the fastest available option.

Reading data from disk is slow, so the search speed can be maximized by pre-loading the entire file into main memory. MICA uses this approach when the sequence occupies up to a predetermined number of chunks, suitably, but not limited to, 16 chunks. The corresponding files usually occupy no more than 3 MB of RAM and can be read from disk in a fraction of a second.

For longer sequences, as described above, MICA sacrifices some potential search speed in exchange for rapid index loading and low memory usage. The only parts of the index that are initially read into memory are the elements that describe the structure of the data arrays. During a search, the position values for the relevant K-mers are selectively read from disk. These read operations are usually the rate-limiting step in the search, but they are relatively efficient because of the compact 2-byte indexing format and because all of the positions for each K-mer are stored contiguously. Only a small portion of the index is used at a given time, so a typical search requires very little memory.

If a query sequence contains a degenerate or otherwise abundant K-mer, then reading the full list of position values for that K-mer might require more RAM than is available. MICA deals with this situation by dividing the subject sequence into segments and searching each segment in turn. During the search of a given segment, only the corresponding K-mer position values are read into memory

EXAMPLES

MICA was coded in C++ and tested on a 2.5-GHz G5 Macintosh running OS X (10.4, Tiger) with 2.5 GB of RAM. As subject data the May 2005 Ensembl release of the human genome was used (Ensemble Genome Browser—ensembl.org/index.html), comprising 3.08 gigabases in 25 files representing the linear chromosomes 1-22, X, and Y, plus the circular mitochondrial chromosome.

Indexing Performance

For a server application, a large index may be acceptable if sufficient memory is available, and slow indexing is acceptable because the index is created once and then used indefinitely. For a desktop application, smaller indexes are desirable because they occupy less disk space. Moreover, versatility is increased if the index can be created and updated rapidly, because this feature facilitates the analysis of new sequences and the modification of existing sequences.

Figure 2:
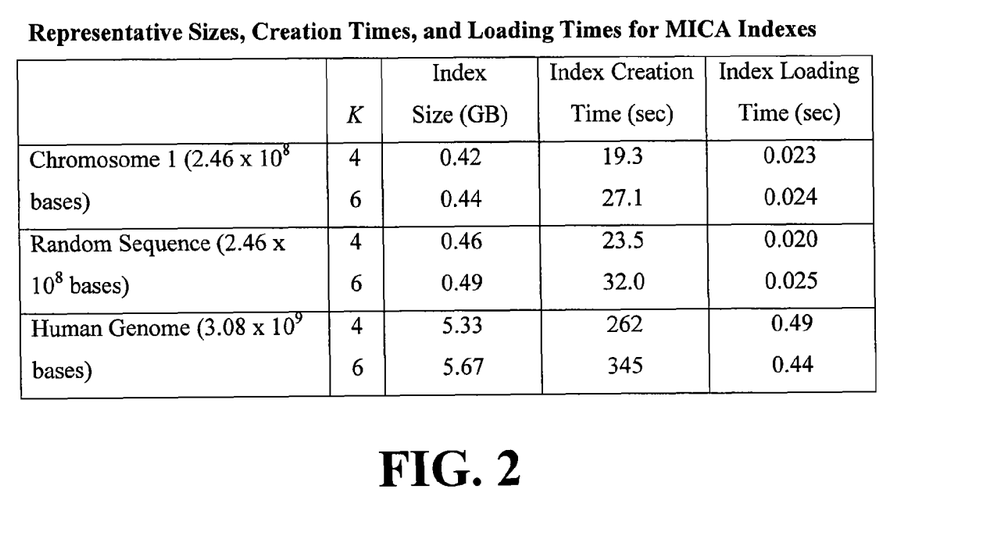
FIG. 2 is a table that depicts representative index sizes, creation times, and loading times of the invention.

FIG. 2 shows representative MICA index sizes and indexing times. The sequences of chromosome 1 and the 25 chromosomes comprising the human genome were obtained from the Ensembl database. A computer-generated random sequence of 246,000,000 bp containing equal proportions of G, A, T, and C was also tested. Index size refers to index elements Index Segment Format, Index Segment Size, Index Properties, Chunk Counts Summary, degenerate K-mer Count, N-Stretch Count (S), Chunk Data Array, Degenerate Data Array, and N-Stretch Data Array of the MICA file (see FIG. 1), and does not include the Sequence Segment. The creation time for each index includes the time needed to write the index to disk, but does not include the additional time needed to embed a copy of the sequence within the file; this additional embedding time for chromosome 1 was 16.4 sec for K=4 or 19.6 sec for K=6. Index loading refers to the reading of elements Segment Format, Segment Size, Sequence Properties, Index Segment Format, Index Segment Size, Index Properties, Chunk Counts Summary, degenerate K-mer Count, and N-Stretch Count (S) of an index from disk into memory. For the human genome, the values listed are the sums of the values for the individual chromosomes.

With human chromosomes, storage requirements for the indexes were just under 2 bytes per base, reflecting the existence of N-stretches in the current genome assembly. With a computer-generated random sequence containing no degenerate base characters, the storage requirement was slightly over 2 bytes per base. The indexing time for chromosome 1, which is 246 million bases, was 19.3 sec for K=4 or 27.1 sec for K=6. Only 56% of the K=6 indexing time (15.3 sec) was due to the indexing procedure itself, with most of the remaining time being consumed by writing the completed index to disk. Indexing the entire human genome required 262 sec (4.4 min) for K=4 or 345 sec (5.8 min) for K=6.

To simulate indexing with limited RAM, MICA indexed chromosome 1 using the procedure that would be followed if only 100 MB of RAM were available. The indexing time for K=6 was 126 sec, which should still be adequate for most applications.

Searching Performance

The subject sequences were chromosome 1 or the entire human genome, and both DNA strands were searched. With the entire genome, the indexes were loaded individually into memory for each search, but the index loading times (FIG. 2) accounted for only a small fraction of the total search times. A series of searches were performed with nondegenerate queries of various lengths and with several partially degenerate queries.

Figure 3:
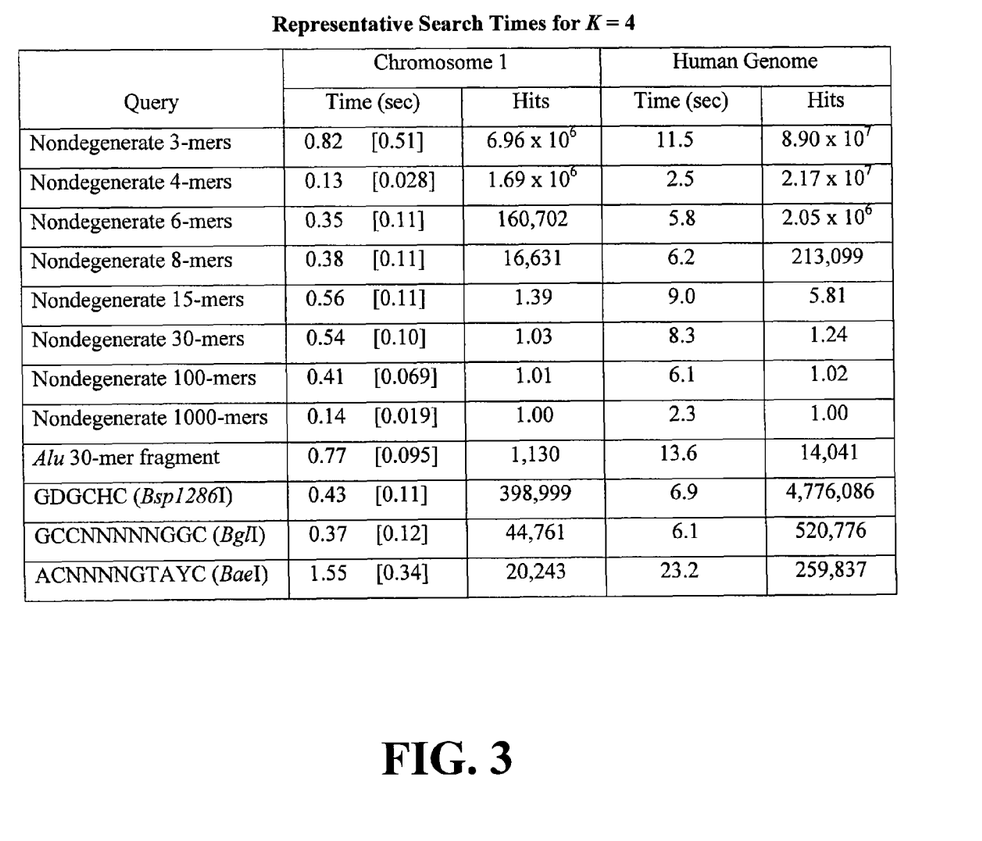
FIG. 3 is a table that depicts representative search times of the invention when K=4.

FIG. 3 shows representative search times for K=4. Both DNA strands were searched using K=4. Results for the 3- to 1000-mer searches are average values obtained by searching with multiple queries. For 3-mers, all 64 possible nondegenerate queries were tested by extending each 3-mer to a partially degenerate 4-mer. For 4-mers, all 256 possible nondegenerate queries were tested. For 6- and 8-mers, 100 randomly chosen nondegenerate queries were tested. In the case of 15- to 1000-mers, each test involved 100 nondegenerate queries that were extracted randomly from chromosome 1 and checked to confirm that a given query had no more than 10 matches in the genome. The Alu 30-mer fragment GGC-CGGGCGCGGTGGCTCACGCCTGTAATC is a conserved sequence found at the 5' ends of Alu repeat elements (See Price A L, Eskin E, Pevzner P A: Whole-genome analysis of Alu repeat elements reveals complex evolutionary history. *Genome Res* 2004, 14:2245-2252, incorporated herein by reference). The three partially degenerate queries are the recognition sequences for the restriction enzymes Bsp1286I, BglI, and BaeI. For chromosome 1, the search times without brackets were obtained after pre-loading only file elements Segment Format, Segment Size, Sequence Properties, Index Segment Format, Index Segment Size, Index Properties, Chunk Counts Summary, degenerate K-mer Count, and N-Stretch Count (S) into memory, and the faster search times with brackets were obtained after pre-loading the entire file. For the entire genome, the search times include the time needed to load elements Segment Format, Segment Size, Sequence Properties, Index Segment Format, Index Segment Size, Index Properties, Chunk Counts Summary, degenerate K-mer Count, and N-Stretch Count (S) of each file into memory. Thus, the data for chromosome 1 reflect the time needed to search a file that is already open, whereas the data for the entire genome reflect the time needed to search a set of unopened files. To ensure that the search times without brackets reflect MICA performance for newly opened indexes, each search was preceded by a large number of extraneous reads, which flushed the main memory of any prior data from the relevant index.

As expected, searches for 4-mers were the fastest, with each search requiring an average of 0.13 sec for chromosome 1 or 2.5 sec for the entire genome. Searches for 6- or 8-mers took about three times as long. For 15-mers, the average search times were 0.56 sec for chromosome 1 or 9.0 sec for the entire genome, about 50% longer than for 8-mers. As the query length increased further, the search times actually decreased as MICA took advantage of rare 4-mers within the queries.

Figure 4:
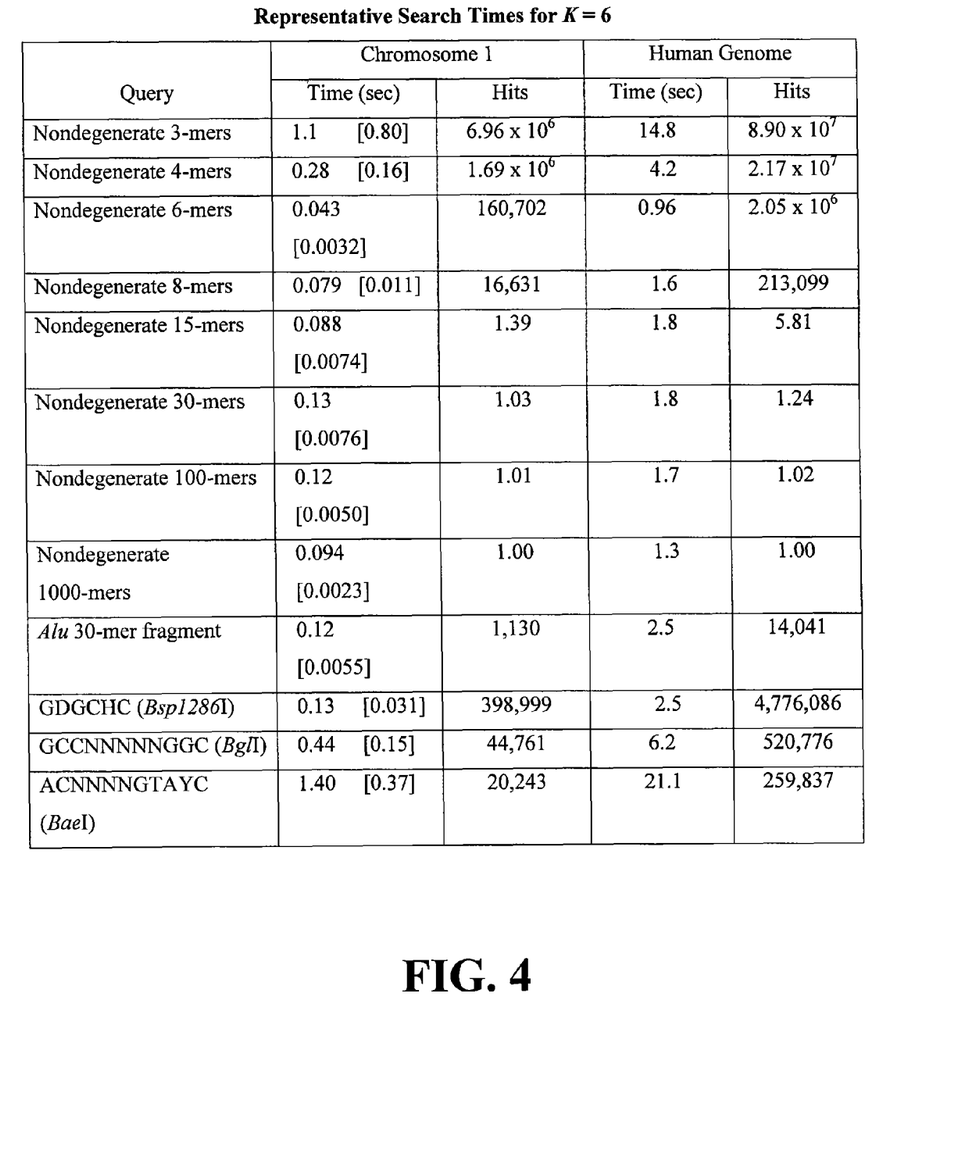
FIG. 4 is a table that depicts representative search time of the invention when K=6.

FIG. 4 shows representative search times for K=6. Both DNA strands were searched using K=6. The queries and the procedure were as described for the experiment set forth in FIG. 3, except that each 3- or 4-mer was extended to a partially degenerate 6-mer.

As expected, searches for 6-mers were the fastest. For 8- to 100-mers, the K=6 searches were approximately five times as fast as the corresponding K=4 searches. The reason for this difference is that read operations are the slowest step for most searches, and an average 6-mer occupies much less index space than an average 4-mer.

When the query length is less than K, the search times are relatively long because multiple K-mer lists must be merged. As an example for K=4, the positions of each 3-mer were found by merging four 4-mer lists, so the 3-mer searches were much slower than the 4-mer searches (FIG. 3). For K=6, the 4-mer searches were much slower than the 6-mer searches, and the 3-mer searches were slower still (FIG. 4). Multiway merges are naturally suited to parallel processing (See Greene W A: k-way merging and k-ary sorts. In: 31*st Annual ACM Southeast Conference:* 1993; Birmingham, Ala.; 1993: 127-135, incorporated herein by reference), and in one embodiment merges can be accelerated by harnessing the enhanced multithreading capacity of newer desktop computers.

For a given query length, searches are fast if there are very few matches to the query, and somewhat slower if multiple matches are distributed throughout the subject sequence. As a test case of a query with many matches, a conserved 30-base fragment of the Alu repeat element was used (See Price A L, Eskin E, Pevzner P A: Whole-genome analysis of Alu repeat elements reveals complex evolutionary history. *Genome Res* 2004, 14:2245-2252, incorporated herein by reference). This Alu fragment was found 1,130 times in chromosome 1 and 14,041 times in the entire genome. The searches for the Alu fragment took only slightly longer than the searches for rare 30-mers (FIGS. 3 and 4). Thus, MICA delivers strong performance even with repeated sequences, which are challenging for some other search algorithms (See Ning A, Cox A J, Mullikin J C: SSAHA: a fast search method for large DNA databases. *Genome Res* 2001, 11:1725-1729, incorporated herein by reference).

To test partially degenerate queries, the recognition sequences of the restriction enzymes Bsp1286I (GDGCHC), BglI (GCCNNNNNGGC), and BaeI (ACNNNNGTAYC) were searched. In the case of BglI, the search involved generating lists of positions for the 3-mers GCC and GGC, and then finding the intersection of those lists. As described above, 3-mer searches require a great deal of calculation time because of the merges, so MICA defers such merges until after the intersection operations. This approach made searching for the BglI recognition sequence about twice as fast as searching for a single 3-mer (FIGS. 3 and 4). The searches for the non-palindromic BaeI recognition sequence were relatively slow because MICA needed to process the data for the 2-mers AC and GT. In general, the most time-consuming searches are those involving K-mers with substantial degeneracy, because multiple individual K-mer lists need to be read from disk and then examined.

Effects of Varying K

Extensive tests with K chosen to be either 4 or 6 were performed. For K=6 the individual K-mer reads were 16-fold smaller on average than for K=4, yet the K=6 searches for typical nondegenerate queries were faster by only about five-fold (FIGS. 3 and 4). The reason for this discrepancy is that the K=6 reads are so small that disk seek times become limiting. Thus, increasing K to 7 would only marginally accelerate searches for typical nondegenerate queries. Moreover, a larger value of K would be detrimental with very short queries and with some partially degenerate queries. For example, when searching for the BglI recognition sequence, MICA expands the 3-mer GCC to the 4-fold degenerate GCCN for K=4, but expands the same 3-mer to the 64-fold degenerate GCCNNN for K=6 or the 256-fold degenerate GCCNNNN for K=7. The best overall compromise for most purposes seems to be K=6.

In the case of DNA molecules such as plasmids for which only a few KB are needed to store the DNA sequence, a K=6 index is excessively large because it requires 24 KB to record how many times each nondegenerate K-mer is present in each chunk. By contrast, a K=4 index requires only 1.5 KB to store this information for a molecule of up to 65,535 bp. Therefore, MICA uses K=4 if the DNA sequence fits within one chunk, or K=6 if the DNA sequence occupies two or more chunks.

Effects of Memory Usage

Figure 5:
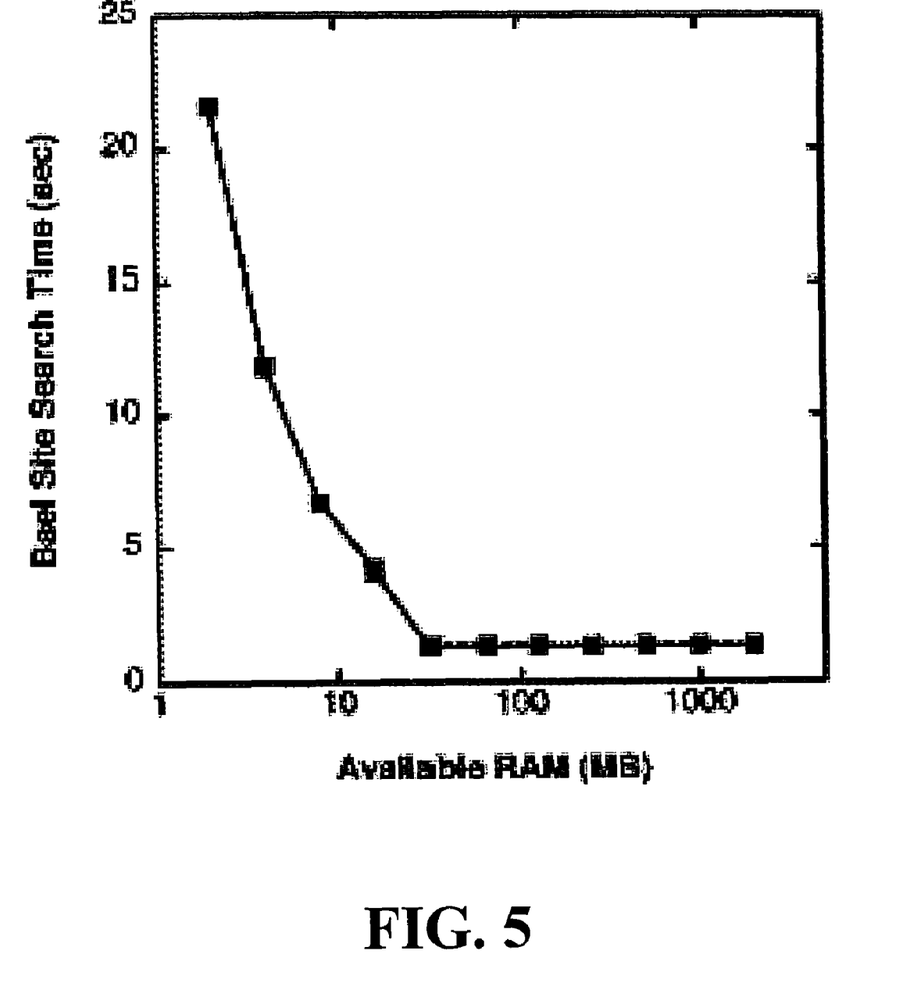
FIG. 5 shows the BaeI Site search time in relation to available RAM.

For the genome-wide searches listed in FIG. 4, the amount of RAM used by MICA ranged from about 1.6 MB for a rare 6-mer to 40 MB for BaeI sites. These numbers are small because the searches were performed one chromosome at a time. To determine how memory limitation affects search times, BaeI sites in chromosome 1 were searched under conditions that simulated different amounts of available RAM (FIG. 5). The memory check algorithm estimated conservatively that searching all of chromosome 1 would require a maximum of 47.4 MB of RAM. As a result, when the available RAM dropped below this level, chromosome 1 was searched in segments. The search speeds decreased accordingly, but this decrease was not severe until the available RAM dropped below about 10 MB. Thus, even with an extensive database containing large chromosomal sequence files, searching can be performed efficiently using a computer with modest amounts of memory.

Because all of the nuclear human chromosomes exceed 1 megabase in length, MICA does not load the full indexes into memory, but instead loads only the elements that describe the structure of the data arrays. The benefits of this strategy are rapid index loading and low memory usage. The disadvantage is that searches are slower than they would be if the full indexes were pre-loaded into memory. To quantify this effect, the test searches were repeated after pre-loading into memory the full MICA files for chromosome 1. The resulting values, listed in brackets in FIGS. 3 and 4, show that pre-loading accelerated the searches. This acceleration was dramatic with nondegenerate queries of length K or more. Yet the pre-loading operation took approximately 18 sec, a prohibitively long time if the goal is to do one or a few quick searches. By avoiding a time-consuming preparatory stage, MICA enables users to search large sequences without delay.

Immediately after indexing, the entire index is typically available in memory, so this time point is convenient for doing any routine searches. As a model for such a routine search, chromosome 1 was indexed using K=6, and then searched for the recognition sequences of the 236 restriction enzymes sold by New England BioLabs. This search was very fast at just under 11 sec.

MICA is designed to be a core indexing and search engine. Because the underlying approach is very simple, the program can be optimized extensively to take advantage of the properties of modern desktop computers. In its present form, MICA is ideally suited to comprehensive searching for exact matches in a DNA database. Such a database might represent, e.g., a genome or a collection of plasmid vectors. Potential applications include: in silico restriction enzyme digestion, which can be used to type organisms by amplified fragment length polymorphism (AFLP) analysis or by pulsed field gel electrophoresis; "virtual PCR" to predict the specificity of PCR amplification from complex templates; and the automated definition of oligonucleotide-flanked sequence-tagged sites (STSs) in genomic sequences. The MICA program can be incorporated into desktop software that allows for versatile browsing and manipulation of DNA sequences. For example, a MICA-based PCR simulator allows us to specify the human genome as a template, and to simulate a PCR amplification from human DNA in 2-3 sec.

The MICA program can be extended by adding alignment algorithms for identifying sequences that are similar but not identical to the query. Such algorithms have been widely studied and implemented (See Gusfield D: Algorithms on Strings, Trees, and Sequences: Computer Science and Computational Biology. Cambridge: Cambridge University Press; 1997; Pearson W R, Lipman D J: Improved tools for biological sequence comparison. *Proc Natl Acad Sci USA* 1988, 85:2444-2448; Altschul SF, Gish W, Miller W, Myers E W, Lipman D J: Basic local alignment search tool. *J Mol Biol* 1990, 215:403-410; Altschul S F, Madden T L, Schaffer A A, Zhang J, Zhang Z, Miller W, Lipman D J: Gapped BLAST and PSI-BLAST: a new generation of protein database search programs. *Nucleic Acids Res* 1997, 25:3389-3402; Hunt E: The suffix sequioa index for approximate string matching. *DCS Tech Report, Dept of Computing Science, University of Glasgow*, dcsglaacuk/publications/PAPERS/7185/TR-2003-135pdf 2003:1-26; Li M, Ma B, Kisman D, Tromp J: Patternhunter II: highly sensitive and fast homology search. *J Bioinform Comput Biol* 2004, 2:417-439; and Noe L, Kucherov G: Improved hit criteria for DNA local alignment. *BMC Bioinformatics* 2004, 5:149, all incorporated herein by reference) and they can benefit greatly from using an index to find "seeds" for the alignments (See Kent W J: BLAT—The BLAST-like alignment tool. *Genome Res* 2002, 12:656-664; Ning Z, Spooner W, Spargo A, Leonard S, Rae M, Cox A: The SSAHA trace server. *Proceedings of the* 2004 *IEEE Compu-*

*tational Systems Bioinformatics Conference (CSB* 2004) 2004:544-545; and Wu T D, Watanabe C K: GMAP: a genomic mapping and alignment program for mRNA and EST sequences. *Bioinformatics* 2005, 21:1859-1875, all incorporated herein by reference). In addition, MICA can easily be modified to operate in server mode. For this purpose, faster searching of large sequences would be achieved by loading the complete indexes into memory, as illustrated in FIGS. 3 and 4.

The invention claimed is:

1. A method of indexing and recording a nucleotide sequence of base length L with a computer to create a file, the method comprising having the computer:
   a) select a nucleotide sequence to index;
   b) separate the nucleotide sequence into C separate chunk sections, where each chunk section contains X bases, wherein X is equal to or less than 65,535 bases, and where C is an integer;
   c) scan the nucleotide sequence, identifying each occurrence of a base sequence of a selected base width K;
   d) determine all of the unique base sequences of width K in the nucleotide sequence, each unique base sequence of width K being a K-mer, a K-mer being either a non-degenerate sequence or partially degenerate sequence;
   e) record in the file the position of each K-mer in the nucleotide sequence.

2. The method of claim 1 wherein C is an integer equal to L/65,535 or the next integer greater than L/65,535.

3. The method of claim 1 wherein C is an integer less than 65,536 and C is an integer equal to L/X or the next integer greater than L/X.

4. The method of claim 1 wherein the position of each non-degenerate K-mer recorded in step e) is recorded in a non-degenerate data array in the file, the non-degenerate data array being divided into $4^K$ partitions corresponding to all of the possible $4^K$ non-degenerate K-mers, each partition containing a list of integers representing the number of times a particular non-degenerate K-mer is present in each of the chunk sections, followed by a list of integers representing intra-chunk section positions of the particular K-mer in each of the chunk sections.

5. The method of claim 1 wherein each partially degenerate K-mer recorded in step e) is recorded in a degenerate data array in the file, wherein each particular partially degenerate K-mer is represented as an integer that marks the absolute position of the particular K-mer, followed by a string that encodes the sequence of the particular K-mer.

6. The method of claim 1 further comprising the steps of having the computer record an integer S representing the number of separate stretches of K or more consecutive N's in the nucleotide sequence and record S pairs of integers that represent the starting positions and lengths of the separate stretches of consecutive N's in the nucleotide sequence.

7. The method of claim 1 further comprising the steps of having the computer:
   determine the number of times each non-degenerate K-mer appears in the nucleotide sequence; and
   record in the file a list of integers representing the total number of times each non-degenerate K-mer appears in the nucleotide sequence.

8. The method of claim 1 further comprising the steps of having the computer:
   determine the total number of partially degenerate K-mers in the nucleotide sequence; and
   record in the file the total number of partially degenerate K-mers in the nucleotide sequence.

9. A method of searching for a specific base sequence in a nucleotide sequence using a computer comprising:
   a) using a computer to access a computer file having:
      (i) a data structure, the data structure containing information regarding the nucleotide sequence, the nucleotide sequence having a length L with a selected indexing window of K bases wide, the nucleotide sequence being in C separate chunk sections, where each chunk section contains X bases, wherein X is equal to or less than 65,535 bases, and where C is an integer, the data structure containing data on K-mers of the nucleotide sequence, a K-mer being either a non-degenerate K-mer or a partially degenerate K-mer;
      (ii) a non-degenerate data array containing the position of each particular non-degenerate K-mer of a nucleotide sequence; and
      (iii) a degenerate data array containing the position of each particular partially degenerate K-mer and a string encoding the sequence of each particular partially degenerate K-mer;
   b) having the computer search the file for the specific base sequence and determining the locations of the specific base sequence; and
   c) displaying the locations of the specific base sequence.

10. A method of searching for a specific base sequence in a nucleotide sequence using a computer having permanent storage and main memory, the method comprising;
   a) having the computer access a data structure being stored in a computer file, the data structure containing information regarding the nucleotide sequence, the data structure containing data on K-mers of the nucleotide sequence, the data structure comprising: a non-degenerate data array containing the position of each particular non-degenerate K-mer of a nucleotide sequence; a degenerate data array containing the position of each particular partially degenerate K-mer and a string encoding the sequence of each particular partially degenerate K-mer; an N-stretch count field containing an integer S representing the number of separate stretches of K or more consecutive N's in the nucleotide sequence; an N-stretch data array containing S pairs of integers that represent the starting positions and lengths of the separate stretches of consecutive N's in the nucleotide sequence; an index properties field containing an integer representing the byte order of the index; a chunk counts summary field containing a list of integers representing the total number of times a particular non-degenerate K-mer appears in the nucleotide sequence; a degenerate K-mer count field containing an integer representing the total number of partially degenerate K-mers in the nucleotide sequence;
   b) having the computer load the index properties field, the chunk counts summary field, the degenerate K-mer count field and the N-stretch count field into main memory;
   c) having the computer divide the specific base sequence into unique K-mers;
   d) having the computer locate K-mer position data for the unique K-mers by accessing information in the fields loaded into main memory in step b) and the information in the degenerate data array, the non-degenerate data array, and the N-stretch data array; and
   e) having the computer use the K-mer position data to determine the location of the specific base sequence in the nucleotide sequence if present.

* * * * *